United States Patent [19]

Feldman

[11] 4,194,511

[45] Mar. 25, 1980

[54] DETECTING CAPACITIVELY COUPLED ECG BASELINE SHIFT

[75] Inventor: Charles L. Feldman, Sudbury, Mass.

[73] Assignee: Electronics for Medicine, Inc., Pleasantville, N.Y.

[21] Appl. No.: 934,883

[22] Filed: Aug. 18, 1978

[51] Int. Cl.² ............................................. A61B 5/04
[52] U.S. Cl. ................................... 128/696; 128/902
[58] Field of Search ................ 128/2.06 B, 2.06 E, 128/696, 639–643, 704, 901, 902

[56] References Cited

U.S. PATENT DOCUMENTS

| | | | |
|---|---|---|---|
| 3,495,584 | 2/1970 | Schwalm | 128/696 |
| 3,608,543 | 9/1971 | Longini et al. | 128/696 |
| 3,868,947 | 3/1975 | Holsinger | 128/901 |
| 3,903,874 | 9/1975 | Shakespeare | 128/704 |
| 4,112,930 | 9/1978 | Feldman et al. | 128/704 |

Primary Examiner—William E. Kamm
Attorney, Agent, or Firm—Charles Hieken

[57] ABSTRACT

In an electrocardiographic system there is a multielement electrode at two skin locations for providing an ECG signal of negligible magnitude between elements because of the close spacing while the pair of elements are sufficiently separated so that the motion of one element is at least partially independent of the motion of the other. Parallel ECG signals are obtained from different elements of two multielement electrodes. The difference between the signals is detected by logical circuitry to produce a signal indicating baseline shift. The elements are coaxial with a 250 K resistor in series with each outer element.

10 Claims, 1 Drawing Figure

DETECTING CAPACITIVELY COUPLED ECG BASELINE SHIFT

BACKGROUND OF THE INVENTION

The present invention relates in general to detecting the baseline shift artifact which contaminates an electrocardiographic signal and more particularly concerns novel apparatus and techniques for detecting that portion of the baseline shift artifact caused by capacitive coupling of charged bodies to the electrodes while retaining the advantages of eliminating the effects of baseline shift artifact resulting from the motion of the electrodes as disclosed in prior copending application Ser. No. 754,538, filed Dec. 27, 1976, now U.S. Pat. No. 4,112,930, and application Ser. No. 917,877 filed June 22, 1978, and entitled APPARATUS AND METHOD FOR EGG BASELINE SHIFT DETECTING.

Although most baseline shift artifact which contaminates an electrocardiographic signal results from motion of the electrodes and the effect of that component is sharply reduced by the inventions disclosed in the aforesaid copending applications, capacitive coupling of external bodies to the electrode wires is a source of additional baseline shift artifact. Patients' clothes, particularly when they are made of synthetic materials that readily develop a substantial static charge, are the most common source of undesired baseline shift artifact capacitively coupled to the electrode wires. This phenomenon of capacitive coupling of charged bodies to the electrodes is particularly severe when patients are much more mobile than patients lying in bed, hard-wired to a bedside monitor.

The voltage generated by the capacitively coupled artifact is directly proportional to the signal source impedance, typically the sum of two electrode-to-skin interfaces plus the impedance produced by the body. Although the impedance is typically less than 50,000 omhs when the electrodes are carefully installed so that the magnitude of the capacitively coupled artifact is correspondingly low, source impedances of 100,000 ohms and greater are not uncommon with a correspondingly higher capacitively coupled artifact.

Accordingly, it is an important object of this invention to provide means and method for detecting capacitively coupled baseline shift artifact.

It is a further object of the invention to achieve the preceding object with apparatus that is relatively easy and inexpensive to fabricate and install.

It is still a further object of the invention to achieve one or more of the preceding objects while maintaining the advantages of the invention disclosed in the aforesaid copending applications.

SUMMARY OF THE INVENTION

According to the invention, there are first and second multielement electrode means attached to first and second surface portions of a patient, each electrode means having elements closely spaced, but insulatedly separated, the ECG potential between the elements being negligible, and the improvement resides in having a relatively large resistance in series with at least one of the elements to significantly increase capacitively coupled artifact produced in the lead connected to that element and assure that the artifact in that lead is greater than the artifact signal produced in the other lead. Preferably, the elements are coaxial and there is a resistance in series with each outer element, typically a 250 K resistor. Preferably the improvement is used in a system having first and second means for differentially combining, respectively, the potentials of one element from each of the multielement electrode means, and the potentials of the other elements from each of the multielement electrode means, to provide first and second ECG signals, and means for differentially combining the ECG signals to provide an artifact signal respesentative of baseline shift including capacitively coupled artifact.

BRIEF DESCRIPTION OF THE DRAWING

Numerous other features, objects and advantages of the invention will become apparent from the following specification when read in connection with the accompanying drawing, the single FIGURE of which is a combined block-pictorial diagram of a system according to the invention.

DETAILED DESCRIPTION OF PREFERRED EMBODIMENTS

Figure 1:
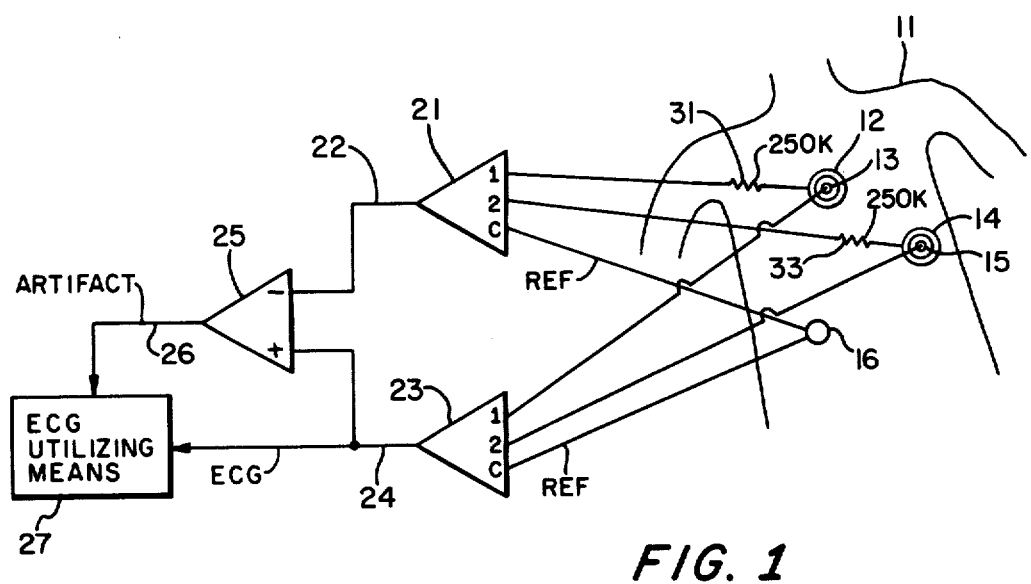

With reference now to the drawing, there is shown a combined block-pictorial diagram of a system according to the invention. A patient 11 has a first multielement electrode having an outer element 12 coaxial about an inner element 13 and a second multielement electrode having an outer electrode 14 coaxial about an inner electrode 15 and a reference electrode 16. The spacing between elements 12 and 13 and between elements 14 and 15 is significantly less than the separation between the first location where elements 12 and 13 are located and the second location where elements 14 and 15 are located and between the first location and the third location where common electrode 16 is located. Typical separation between elements 12 and 13 and between elements 14 and 15 is 1 inch or less. The separation between elements in a multielement electrode is small enough so that the ECG potential between them is negligible and large enough so that the motion of one electrode is at least partially independent of the motion of the other. Electrode elements 12, 14, and 16 are connected to amplifier 21 with lines 41,42, and 43, respectively, and electrode elements 13,15 and 16 are connected to amplifier 22 with lines 44,45, and 46 respectively.

The system includes a first ECG differential amplifier 21 for providing a first ECG signal on line 22, and a second ECG differential amplifier 23 for providing a second ECG signal on line 24. It also includes a differential combiner 25, which need not be an amplifier, for providing an artifact signal on line 26. Differential combiner 25 receives the signals on line 22 and 24. ECG utilizing means 27 receives the signals on lines 24 and 26 and typically provides an alarm signal only when the ECG signal characterizes an unstable condition of patient 14, such as arrythmia or an unacceptable heart rate, while preventing the occurrence of an alarm signal when an artifact signal on line 26 occurs, signifying that a condition has occurred at an associated pair of elements producing a baseline shift or that there is artifact capacitively coupled to one or more of the lines.

The grounded, common or reference input C of each differential amplifier 21 and 23 is connected to one or more reference electrodes 16 at the third patient surface location. It is common practice to have a reference terminal such as 16 attached to the patient and connected to one or more common terminals of the amplifying means for reducing noise. The 1 and 2 signal inputs of first ECG differential amplifier 21 are connected to outer elements 12 and 14, respectively, through resistors 31 and 33, respectively, the elements being selected from different multielement electrodes at different patient locations. Typically, the value of resistors 31 and 33 are selected so their sum is equal to or larger than the sum of the resistance between two electrode/patient interfaces and the patient resistance. This assures that the capacitively coupled artifact appearing at amplifier 21 will be larger than that appearing at amplifier 23. Typical values are 250 K ohms for each of resistors 31 and 33. The 1 and 2 signal inputs of the second ECG differential amplifier 23 are connected to the other elements 13 and 15, respectively, of the different multielement electrodes.

Accordingly, two nearly equal ECG signals on lines 22 and 24 from the two multielement electrodes are produced. The difference between the two parallel ECG signals, as detected by differential combiner 25, is baseline shift, creating the artifact signal on line 26.

The specific means for utilizing the ECG signals 22 and 24 and the artifact 26 is not a part of the invention. For example, it is possible to use either of the ECG signals on lines 22 and 24 or to combine the two by summation to produce an average ECG. Or ECG utilizing means 27 may include, in addition, circuitry that responds to the occurrence of an artifact signal on line 26 for providing a signal that inhibits the alarm indicating circuitry. The ECG utilizing means 27 might also or alternatively include circuitry for combining the artifact signal with the ECG signal to effectively restore the shifted baseline substantially to the normal baseline 12.

A feature of the present invention is that resistors 31 and 33 assure that appreciable baseline shift artifact caused by capacitive coupling of external bodies to the electrode wires that might not be detected by the invention disclosed in the aforesaid copending applications will now appear on line 26. While the preferred form of the invention is shown in the drawing with large resistors of equal value respectively connected to the outer electrodes, it is within the principles of the invention to use a single resistor having a value equal to the sum of the two connected to a single outer electrode element, or to a single inner electrode element or to any single electrode element in the case of noncoaxial elements. It is also within the principles of the invention to divide the resistance among all the electrodes or part of them. The resistance is preferably high enough to assure unbalanced capacitive coupling and typically greater than the source impedance at an electrode but not so great that the resistance introduces significant attenuation. An acceptable range of resistance is from 100 K ohms per pair of electrodes to 1 M ohms per pair of electrodes. It is also preferred that the resistors be physically located close to the electrodes. The resistance could be introduced by high resistance leads or a combination of high resistance leads and fixed resistors.

There ha; been described novel apparatus and techniques for significantly increasing capacitively coupled baseline shift artifact to insure its detection. It is evident that those skilled in the art may now make numerous uses and modifications of and departures from the specific embodiments described herein without departing from the inventive concepts. Consequently, the invention is to be construed as embracing each and every novel feature and novel combination of features present in or possessed by the apparatus and techniques herein disclosed and limited solely by the spirit and scope of the appended claims.

What is claimed is:

1. In apparatus for providing an ECG signal having first and second multielement electrode means each having elements closely spaced but insulatedly separated for connection to respective surface portions of a patient with the ECG potential between said elements being negligible, the improvement comprising,
   resistive means in series with at least one of said elements of sufficiently high resistance to significantly unbalance capacitively coupled baseline shift artifact.

2. The improvement in accordance with claim 1 wherein said elements are coaxial.

3. The improvement in accordance with claim 2 wherein said resistive means comprises first and second resistors of substantially the same value connected to respective elements in respective electrode means.

4. The improvement in accordance with claim 3 wherein the resistances are connected to respective outer elements.

5. The improvement in accordance with claim 3 wherein said resistive means comprises a single resistance connected to an outer element.

6. In apparatus for providing an ECG signal and detecting baseline shift in said ECG signal having a first multielement electrode means having elements closely spaced but insulatedly separated for connection to a first surface portion of a patient with the ECG potential between said elements being negligible, a second multielement electrode means having elements closely spaced but insulatedly separated for connection to a second surface portion of said patient with the ECG potential between the latter elements being negligible, first means for differentially combining the potentials of one element of said first multielement electrode means and one element of said second multielement electrode means for providing a first ECG signal, second means for differentially combining the potentials of another element of said second multielement electrode means for providing a second ECG signal, and means for differentially combining said first and second ECG signals to provide an artifact signal representative of baseline shift in said ECG signals, the improvement comprising,
   resistive means in series with at least one of said elements of resistance sufficiently high for significantly unbalancing capacitively coupled baseline shift artifact.

7. The improvement in accordance with claim 6 wherein said elements are coaxial.

8. The improvement in accordance with claim 7 wherein said resistive means comprises first and second resistors of substantially the same value connected to respective elements in respective electrode means.

9. The improvement in accordance with claim 8 wherein the resistances are connected to respective outer elements.

10. The improvement in accordance with claim 8 wherein said resistive means comprises a single resistance connected to an outer element.

* * * * *